United States Patent
Pugh (10) Patent No.: US 9,801,560 B2
(45) Date of Patent: Oct. 31, 2017

(54) OPHTHALMIC LENS WITH A NEURAL FREQUENCY DETECTION SYSTEM

(71) Applicant: Johnson & Johnson Vision Care, Inc., Jacksonville, FL (US)

(72) Inventor: Randall Braxton Pugh, St. Johns, FL (US)

(73) Assignee: Johnson & Johnson Vision Care, Inc., Jacksonville, FL (US)

( * ) Notice: Subject to any disclaimer, the term of this patent is extended or adjusted under 35 U.S.C. 154(b) by 884 days.

(21) Appl. No.: 14/011,307

(22) Filed: Aug. 27, 2013

(65) Prior Publication Data

US 2015/0065905 A1 Mar. 5, 2015

(51) Int. Cl.
*A61B 5/04* (2006.01)
*A61B 5/0478* (2006.01)
*A61B 5/00* (2006.01)
*G02C 7/04* (2006.01)
*G02C 7/08* (2006.01)

(52) U.S. Cl.
CPC ........ *A61B 5/04001* (2013.01); *A61B 5/0478* (2013.01); *A61B 5/6821* (2013.01); *A61B 5/0006* (2013.01); *A61B 5/0022* (2013.01); *A61B 5/7225* (2013.01); *A61B 5/7405* (2013.01); *A61B 5/7445* (2013.01); *A61B 2560/0214* (2013.01); *A61B 2560/0219* (2013.01); *A61B 2562/0209* (2013.01); *A61B 2562/0228* (2013.01); *G02C 7/04* (2013.01); *G02C 7/083* (2013.01)

(58) Field of Classification Search
CPC ............................ A61B 5/0478; A61B 5/6821
See application file for complete search history.

(56) References Cited

U.S. PATENT DOCUMENTS

| | | | |
|---|---|---|---|
| 5,251,627 | A | 10/1993 | Morris |
| 7,631,968 | B1 | 12/2009 | Dobson et al. |
| 2007/0019279 | A1 | 1/2007 | Goodall et al. |
| 2008/0130867 | A1 | 6/2008 | Bowen |

(Continued)

FOREIGN PATENT DOCUMENTS

| WO | WO 2010051203 A1 | 5/2010 |
|---|---|---|
| WO | WO 2012125425 A2 | 9/2012 |
| WO | WO 2012125425 A3 | 9/2012 |

OTHER PUBLICATIONS

PCT International Search Report for PCT/US2014/052488 Date of Mailing Feb. 6, 2015 Date of Completion Feb. 18, 2015.

(Continued)

*Primary Examiner* — Christian Jang (57) ABSTRACT

The present invention relates generally to an ophthalmic device capable of monitoring neural frequencies and correlating the measured frequencies them to specific brain activity/functions. In some embodiments, profiles specific to the user of the ophthalmic device can be pre-programmed to tailor a brain activity/function profiles according to a user. Based on the determined brain activity/function from the correlation, a signal may be generated to provide feedback to the user. The signal may be transmitted to the user in one or more form. For example, the signal may be outputted to a wireless device in wireless communication with the ophthalmic device, and/or through an audible signal projected by an acoustic element, and/or a visual signal projected using a photon emitter, both which may be included in the ophthalmic device.

20 Claims, 8 Drawing Sheets

(56) References Cited

U.S. PATENT DOCUMENTS

| | | |
|---|---|---|
| 2010/0067723 A1 | 3/2010 | Bergmann et al. |
| 2010/0103369 A1 | 4/2010 | Pugh et al. |
| 2010/0142740 A1 | 6/2010 | Roerup |
| 2011/0158444 A1 | 6/2011 | Waldmann |
| 2012/0199995 A1 | 8/2012 | Pugh |
| 2012/0236524 A1 | 9/2012 | Pugh et al. |
| 2012/0242953 A1 | 9/2012 | Pugh et al. |

OTHER PUBLICATIONS

PCT International Search Report for PCT/U52014/052486 Date of Completion Oct. 29, 2014 dated Nov. 19, 2014.

OPHTHALMIC LENS WITH A NEURAL FREQUENCY DETECTION SYSTEM

FIELD OF THE INVENTION

This invention describes an energized Ophthalmic Device with a neural frequency detection system, and more specifically, the neural frequency detection system forming part of the Ophthalmic Device and being configured to correlate measured frequencies to recognized pre-determined frequency patterns associated with a brain function and/or activity.

BACKGROUND OF THE INVENTION

Traditionally, an ophthalmic device, such as a contact lens, an intraocular lens, or a punctal plug, included a biocompatible device with a corrective, cosmetic, or therapeutic quality. A contact lens, for example, may provide one or more of vision correcting functionality, cosmetic enhancement, and therapeutic effects. Each function is provided by a physical characteristic of the lens. A design incorporating a refractive quality into a lens may provide a vision corrective function. A pigment incorporated into the lens may provide a cosmetic enhancement. An active agent incorporated into a lens may provide a therapeutic functionality. Such physical characteristics are accomplished without the lens entering into an energized state. An ophthalmic device has traditionally been a passive device.

Novel ophthalmic devices based on energized ophthalmic inserts have recently been described. These devices may use the energization function to power active optical components. For example, a wearable lens may incorporate a lens assembly having an electronically adjustable focus to augment or enhance performance of the eye.

Moreover, as electronic devices continue to be developed and miniaturized, it is becoming increasingly more likely to create wearable or embeddable microelectronic devices for a variety of uses. For example, in one unrelated field, the study of brain activity through frequency analysis has been rapidly growing. Typically in these studies researchers place electrodes on the scalp and measure brainwaves that are produced by neurons. The measured brainwaves are used to identify patterns and correlate them to specific brainwave frequencies resulting from a specific brain activity/function. Some of the techniques that have been explored to monitor the brain function/activity and record brainwave data include electrocorticography and electroencephalography. Using these techniques, researchers have been able to monitor consciousness in patients with traumatic injuries, and in studies of epilepsy and sleep, for example.

Frequency recognition software has also been improved over time. For example, in speech recognition software, the software can make deductions about what a specific person is saying with only limited prior analysis of certain words. The specific pre-recorded frequencies of those words can be used to deduct additional frequencies/words without having to pre-record those. Accordingly, with the quickly developing frequency recognition software and brainwave study techniques and studies, it is desired to come up with new devices and associated methods that can be used to analyze and monitor brainwaves in useful manners.

SUMMARY OF THE INVENTION

The foregoing needs are met, to a great extent, by the present invention, wherein in one aspect an energized Ophthalmic Device with a neural frequency detection system is disclosed. The neural frequency detection system which can be used to monitor and provide and alert to the user according to an identified brain activity/function determined from the analysis of brainwave patterns.

According to some aspects of the disclosure, an ophthalmic device with neural frequency detection is disclosed. The Ophthalmic lens can include a Media Insert comprising a front curve arcuate surface and a back curve arcuate surface, wherein the front curve arcuate surface and the back curve arcuate surface form a cavity capable of containing an Energy Source dimensioned to conform to an area within the cavity. The Energy Source can be in electrical connection and capable of Energizing a controller comprising a computer processor in digital communication with a digital media storage device storing software code, a transmitter in logical communication with the processor and also in logical communication with a communication network, and the software being executable upon demand and operative with the processor to: receive a signal through the communication network from one or more sensors capable of measuring neural frequencies and sending one or more measured neural frequencies through the communication network, and correlate the one or more measured neural frequencies with a brain function/activity using pre-recorded data in the media storage device.

In additional aspects of the disclosure, a method of detecting brain activity using an ophthalmic device is disclosed. The method including: providing an ophthalmic device with a neural frequency detection system comprising an Energy Source in electrical connection and capable of Energizing a controller comprising a computer processor, a digital media storage device, a transmitter in logical communication with the processor and also in logical communication with a communication network; recording in the digital media storage device neural frequency profiles for a plurality of brain functions; receiving a signal through the communication network from one or more sensors capable of measuring neural frequencies and sending one or more measured neural frequencies through the communication network; and correlating the one or more measured neural frequencies with a brain function using said pre-recorded data in the media storage device.

In yet additional aspects of the disclosure, the method of detecting brain activity can include providing an ophthalmic device with neural frequency detection system comprising an Energy Source in electrical connection and capable of Energizing a controller comprising a computer processor, a digital media storage device, a transmitter in logical communication with the processor and also in logical communication with a communication network; receiving a signal through the communication network from one or more sensors capable of measuring neural frequencies and sending one or more measured neural frequencies through the communication network; and correlating the one or more measured neural frequencies with a brain function.

BRIEF DESCRIPTION OF THE DRAWINGS

The foregoing and other features and advantages of the invention will be apparent from the following, more particular description of preferred embodiments of the invention, as illustrated in the accompanying drawings.

DETAILED DESCRIPTION OF THE INVENTION

The disclosure will now be described with reference to the drawing figures, in which like reference numerals refer to like parts throughout.

Various aspects of the Ophthalmic Device and method disclosed may be illustrated by describing components that are coupled, sealed, attached, and/or joined together. As used herein, the terms "coupled", "sealed", "attached", and/or "joined" are used to indicate either a direct connection between two components or, where appropriate, an indirect connection to one another through intervening or intermediate components. In contrast, when a component is referred to as being "directly coupled", "directly sealed", "directly attached", and/or "directly joined" to another component, there are no intervening elements present.

Relative terms such as "lower" or "bottom" and "upper" or "top" may be used herein to describe one element's relationship to another element illustrated in the drawings. It will be understood that relative terms are intended to encompass different orientations in addition to the orientation depicted in the drawings. By way of example, if aspects of an exemplary Ophthalmic Device shown in the drawings are turned over, elements described as being on the "bottom" side of the other elements would then be oriented on the "top" side of the other elements. The term "bottom" can therefore encompass both an orientation of "bottom" and "top" depending on the particular orientation of the apparatus.

Various aspects of an Ophthalmic Device with a neural frequency detection system may be illustrated with reference to one or more exemplary embodiments. As used herein, the term "exemplary" means "serving as an example, instance, or illustration," and should not necessarily be construed as preferred or advantageous over other embodiments disclosed herein.

GLOSSARY

In this description and claims directed to the disclosed invention, various terms may be used for which the following definitions will apply:

Energized: as used herein refers to the state of being able to supply electrical current to or to have electrical energy stored within.

Energy: as used herein refers to the capacity of a physical system to do work. Many uses within this disclosure may relate to the said capacity being able to perform electrical actions in doing work.

Energy Source: as used herein refers to a device or layer that is capable of supplying Energy or placing a logical or electrical device in an Energized state.

Energy Harvester: as used herein refers to a device capable of extracting energy from the environment and converting it to electrical energy.

Functionalized: as used herein refers to making a layer or device able to perform a function including for example, energization, activation, or control.

Leakage: as used herein refers to unwanted loss of energy.

Ophthalmic Device: as used herein refers to any device that resides in or on the eye. These devices may provide optical correction, may be cosmetic, or may provide functionality unrelated to the eye. For example, the term lens may refer to a contact lens, intraocular lens, overlay lens, ocular insert, optical insert, or other similar device through which vision is corrected or modified, or through which eye physiology is cosmetically enhanced (e.g. iris color) without impeding vision. Alternatively, the Lens may provide non-optic functions such as, for example, monitoring glucose, delivering sound signals and/or administrating medicine. In some embodiments, the preferred lenses of the invention are soft contact lenses are made from silicone elastomers or hydrogels, which include, for example, silicone hydrogels, and fluorohydrogels.

Lithium Ion Cell: as used herein refers to an electrochemical cell where Lithium ions move through the cell to generate electrical energy. This electrochemical cell, typically called a battery, may be reenergized or recharged in its typical forms.

Media Insert: as used herein refers to an encapsulated insert that will be included in an energized ophthalmic device. The energization elements and circuitry may be incorporated in the Media Insert. The Media Insert defines the primary purpose of the energized ophthalmic device. For example, in embodiments where the energized ophthalmic device allows the user to adjust the optic power, the Media Insert may include energization elements that control a liquid meniscus portion in the Optical Zone. Alternatively, a Media Insert may be annular so that the Optical Zone is void of material. In such embodiments, the energized function of the Lens may not be optic quality but may be, for example, monitoring glucose, sound delivery, and/or administering medicine.

Operating Mode: as used herein refers to a high current draw state where the current over a circuit allows the device to perform its primary energized function.

Optical Zone: as used herein refers to an area of an ophthalmic lens through which a wearer of the ophthalmic lens sees.

Power: as used herein refers to work done or energy transferred per unit of time.

Rechargeable or Re-energizable: as used herein refers to a capability of being restored to a state with higher capacity to do work. Many uses within this invention may relate to the capability of being restored with the ability to flow electrical current at a certain rate and for a certain, reestablished period.

Reenergize or Recharge: as used herein refers to restoring to a state with higher capacity to do work. Many uses within this invention may relate to restoring a device to the capability to flow electrical current at a certain rate and for a certain, reestablished period.

Reference: as use herein refers to a circuit which produces an, ideally, fixed and stable voltage or current output suitable for use in other circuits. A reference may be derived from a bandgap, may be compensated for temperature, supply, and process variation, and may be tailored specifically to a particular application-specific integrated circuit (ASIC).

Reset Function: as used herein refers to a self-triggering algorithmic mechanism to set a circuit to a specific predetermined state, including, for example, logic state or an energization state. A Reset Function may include, for example, a power-on reset circuit, which may work in conjunction with the Switching Mechanism to ensure proper bring-up of the chip, both on initial connection to the power source and on wakeup from Storage Mode.

Sleep Mode or Standby Mode: as used herein refers to a low current draw state of an energized device after the Switching Mechanism has been closed that allows for energy conservation when Operating Mode is not required.

Stacked: as used herein means to place at least two component layers in proximity to each other such that at least a portion of one surface of one of the layers contacts a first surface of a second layer. In some embodiments, a film, whether for adhesion or other functions may reside between the two layers that are in contact with each other through said film.

Stacked Integrated Component Devices or SIC Devices: as used herein refers to the products of packaging technologies that assemble thin layers of substrates that may contain electrical and electromechanical devices into operative-integrated devices by means of stacking at least a portion of each layer upon each other. The layers may comprise component devices of various types, materials, shapes, and sizes. Furthermore, the layers may be made of various device production technologies to fit and assume various contours.

Storage Mode: as used herein refers to a state of a system comprising electronic components where a power source is supplying or is required to supply a minimal designed load current. This term is not interchangeable with Standby Mode.

Substrate Insert: as used herein refers to a formable or rigid substrate capable of supporting an Energy Source within an ophthalmic lens. In some embodiments, the Substrate insert also supports one or more components.

Switching Mechanism: as used herein refers to a component integrated with the circuit providing various levels of resistance that may be responsive to an outside stimulus, which is independent of the ophthalmic device.

Recent developments in Ophthalmic Devices including, for example, contact lenses, have occurred enabling Functionalized Ophthalmic Devices that can be Energized. The Energized Ophthalmic Device can comprise the necessary elements to correct and/or enhance the vision of users using embedded micro-electronics. Additional functionality using micro-electronics can include, for example, variable vision correction, tear fluid analysis, and/or visual and/or audio feedback to the user.

In unrelated fields, appreciation of brainwave detection and uses of neural signals, including correlation to a wide range of perceptual and cognitive brain functions, has been rapidly developing. Neural signals can be recognized as electrical activities of the brain measurable at different frequencies. They can typically be detected at different areas of the brain and described as low frequency bands at delta (<4 Hx), theta (4-8 Hz), alpha (8-12 Hz), and beta (12-30 Hz) to high frequencies at gamma band that spans from roughly gamma (30-80 Hz) to high gamma (>80 Hz). Currently, detection of brainwave frequencies routinely takes place by attaching sensors to the scalp of a patient or using invasive probes during surgeries. The detection is limited, however, due to the low frequency bands that the brainwaves emit from the neurons which require that the sensors of the device be in direct contact with brain tissue or include a conductive liquid or gel.

With the use of nano-electronics, and in accordance to one aspect of the disclosure, a neural frequency detection system can be incorporated in an Energized Ophthalmic Device. By incorporating a neural frequency detection system in the ophthalmic environment, the brainwave sensors can be both in very close proximity to the frontal lobe part of the brain and may rest in an aqueous or wet environment, i.e. ocular fluid, increasing the sensitivity of the sensors. In addition, because the frontal lobe part of the brain includes most of the dopamine-sensitive neurons in the cerebral cortex, better brain function determinations with regards to a person's attention, reward, short-term memory tasks, planning, and motivation can be made. More importantly, the determinations may be made implementing an innocuous Ophthalmic Device that can be worn by a user without the need of wires.

In additional aspects of the disclosure, brainwave monitoring can be used to provide feedback and/or as a control means for a device in wireless communication with the Ophthalmic Device. Feedback may include communicating to the user brain activity/function without delay, for example, via audible and/or visual signals provided directly by the Ophthalmic Device or using a wireless device in wireless communication with the Ophthalmic Device. The audible signal can be communicated with an Ophthalmic Device with sound generating elements that can be used to communicate the audio signals through bone conduction through the eye socket to the cochlea of the inner ear. This type of device has been disclosed on U.S. patent application No. 14/011,230, titled "Ophthalmic Device with Micro-Acoustic Elements" disclosed by the same inventive entity of the present disclosure. In addition, the Ophthalmic Device may include photonic elements, such as an LED array, that may be used to provide a visual signal to the user. In yet additional embodiments, the signals may be communicated through an interface of the wireless device in communication with the Ophthalmic Device.

The feedback generated using the monitored brain frequencies may include a message, beep, light alert, and/or both. This feedback may alert the user, for example, when the user loses focus/attention while he/she is performing a specific task. This may include, for example, a visual/sound alert that is communicated to the user while he is driving and loses focus. Alternatively or in addition to, the monitoring of brain frequencies may be used, for example, to monitor a personal motivation to accomplish an action and control a processor accordingly. For example, this may be used for a person to communicate a desire and control a robotic hand. The control can be useful in a range of applications including a paralyzed person trying move something, a surgeon who is operating a robotic hand during an operation, and the such.

In yet additional embodiments, two Ophthalmic Devices being worn by two different individuals and in wireless communication with each other may be used to communicate messages between the two wearers, i.e. synthetic telepathy. This can be done, for example, in cases where private local communication is desired through a secure local area network. This can be implemented in military cases using coded messages, for example.

Figure 1:
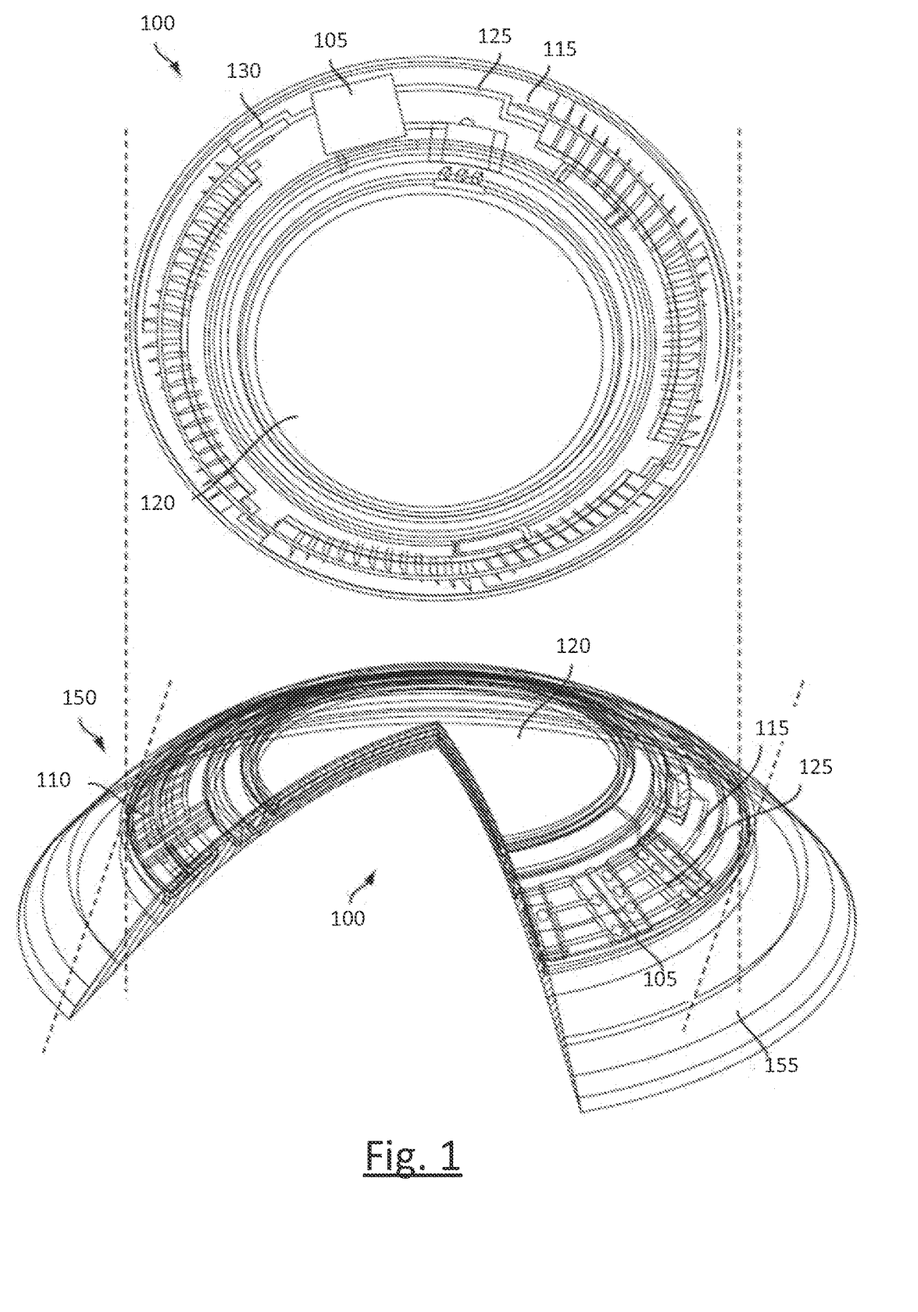
FIG. 1 is a diagrammatic representation of a first exemplary Energized Ophthalmic Device comprising both optics and a neural frequency detection system in accordance with aspects of the present disclosure.

Referring now to FIG. 1, a diagrammatic representation of a first exemplary Energized Ophthalmic Device 150 comprising both optics and a neural frequency detection system in accordance with aspects of the present disclosure is depicted. A top view of an exemplary Media Insert 100 for an Energized Ophthalmic Device 150 that can include a neural frequency detection system 105 and an isometric exemplary energized Ophthalmic Device 150 including the Media Insert 100 are depicted. The Media Insert 100 may comprise an Optical Zone 120 that may or may not be functional to provide vision correction. Where the energized function of the ophthalmic device is unrelated to vision, the Optical Zone 120 of the Media Insert 100 may be void of material. In some embodiments, the Media Insert 100 may include a portion outside of the Optical Zone 120 comprising a substrate 115 incorporated with Energization Elements and electronic components forming part of the neural frequency detection system 105 which include one or more low band frequency sensors. In some embodiments, for example, the one or more sensors may include silicon nanowires capable of providing low power and high sensitivity.

In addition in some embodiments, a power source 110, for example, a battery, and a load, which may be a semiconductor die may also be attached to the Media Insert 115. Conductive traces 125 and 130 may electrically interconnect the electronic components of the neural frequency detection system 105 and the energization elements 110. In some embodiments, the Media Insert 100 can be fully encapsulated to protect and contain the energization elements 110, traces 125 and 130, and electronic components of the neural frequency detection system 105. In some embodiments, the encapsulating material may be semi-permeable, for example, to prevent specific substances, such as water, from entering the Media Insert 100 and to allow specific substances, such as ambient gasses, fluid samples, and/or the byproducts of reactions within energization elements 110, to penetrate and/or escape from the Media Insert 100. In embodiments where the Media Insert 100 is permeable or semi-permeable, the sensors or sensor's contacts (not shown) of the neural frequency detection system 105 can be positioned on the Media Insert's surface to allow direct contact with the ocular surface and ocular fluid on which the Ophthalmic Device rests on.

The Media Insert 100 may be included in/or on an Ophthalmic Device 150, which may also comprise a polymeric biocompatible material. The Ophthalmic Device 150 may include a rigid center, soft skirt design wherein a central rigid optical element comprises the Media Insert 100. In some specific embodiments, the Media Insert 100 may be in direct contact with the atmosphere and/or the corneal surface on respective anterior and posterior surfaces, or alternatively, the Media Insert 100 may be encapsulated in the Ophthalmic Device 150. The periphery 155 of the Ophthalmic Device 150 may be a soft skirt material, including, for example, a hydrogel material. For example, the Ophthalmic Device 150, may be an Energized soft hydrogel contact lens and can include a silicone containing component. A "silicone-containing component" is one that contains at least one [—Si—O—] unit in a monomer, macromer or prepolymer. Preferably, the total Si and attached O are present in the silicone-containing component in an amount greater than about 20 weight percent, and more preferably greater than 30 weight percent of the total molecular weight of the silicone-containing component. Useful silicone-containing components preferably comprise polymerizable functional groups such as acrylate, methacrylate, acrylamide, methacrylamide, vinyl, N-vinyl lactam, N-vinylamide, and styryl functional groups.

The infrastructure of the Media Insert 100 and the Ophthalmic Device 150 can provide a superior environment to perform analysis of neural emitted frequencies since the sensors can be in contact with an ocular surface and ocular fluid, which are conductive by nature. Conductive types of ocular fluid can include any one, or a combination of: tear fluid, aqueous humour, vitreous humour, and other interstitial fluids located in the eye.

Figure 2:
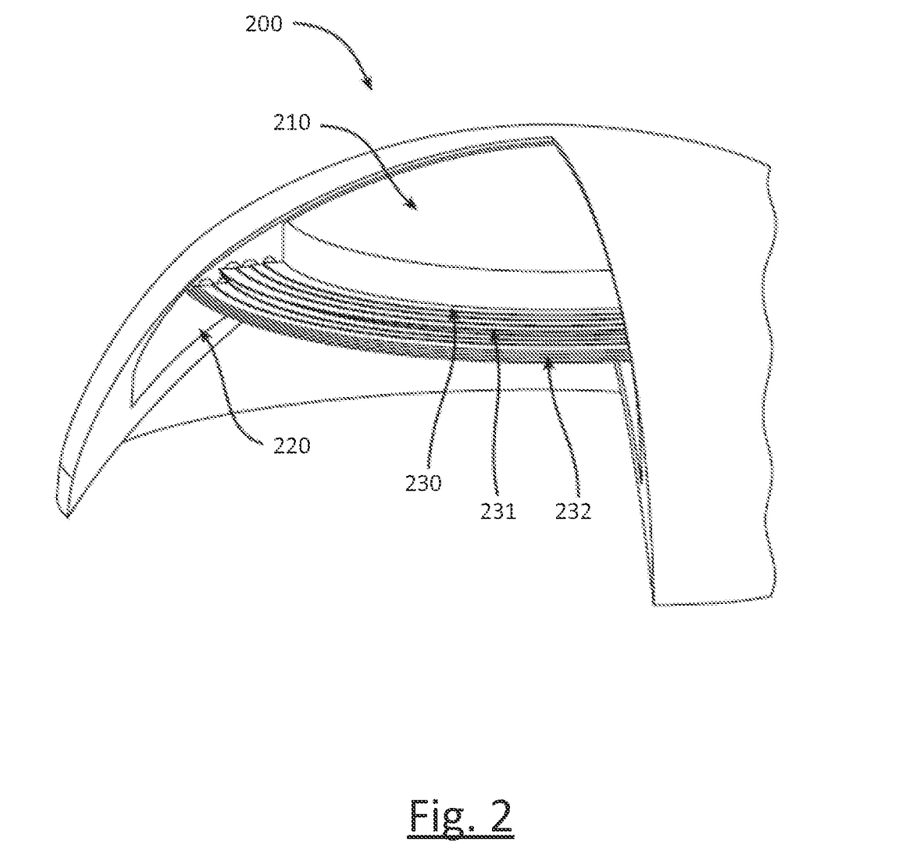
FIG. 2 is a diagrammatic representation of a second exemplary Energized Ophthalmic Device comprising both optics and a neural frequency detection system in accordance with aspects of the present disclosure.

Referring now to FIG. 2, a diagrammatic representation of a second exemplary energized ophthalmic device comprising both optics and a neural frequency detection system in accordance with aspects of the present disclosure is depicted. In particular, a three dimensional cross section representation of an exemplary Ophthalmic Device 200 including a Functionalized Layer Media Insert 220 configured to include the neural frequency detection system on one or more of its Stacked Integrated Component Layers 230, 231, 232 is illustrated. In the present exemplary embodiment, the Media Insert 220 surrounds the entire periphery of the Ophthalmic Device 200. One skilled in the art can understand that the actual Media Insert 220 may comprise a full annular ring or other shapes that still may reside inside or on the hydrogel portion of the Ophthalmic Device 200 and be within the size and geometry constraints presented by the ophthalmic environment of the user.

Layers 230, 231 and 232 are meant to illustrate three of numerous layers that may be found in a Media Insert 220 formed as a stack of functional layers. In some embodiments, for example, a single layer may include one or more of: active and passive components and portions with structural, electrical or physical properties conducive to a particular purpose including the Communication System functions described in the present disclosure. Furthermore, in some embodiments, a layer 230 may include an Energy Source, such as, one or more of: a battery, a capacitor and a receiver within the layer 230. Item 231 then, in a non-limiting exemplary sense may comprise microcircuitry in a layer that detects actuation signals for the Ophthalmic Device 200. In some embodiments, a power regulation layer 232, may be included that is capable of receiving power from external sources, charges the battery layer 230 and controls the use of battery power from layer 330 when the Ophthalmic Device 200 is not in a charging environment. The power regulation may also control signals to an exemplary active lens, demonstrated as item 210 in the center annular cutout of the Media Insert 220.

As previously mentioned, an Energized Ophthalmic Device 200 with an embedded Media Insert 220 may include an energy source, such as an electrochemical cell or battery as the storage means for the energy and in some embodiments, encapsulation, and isolation of the materials comprising the energy source from an environment into which an Ophthalmic Device 200 is placed. In some embodiments, a Media Insert 220 can also include a pattern of circuitry, components, and energy sources. Various embodiments may include the Media Insert 220 locating the pattern of circuitry, components and Energy Sources around a periphery of an Optical Zone 210 through which a wearer of an Ophthalmic Lens would see, while other embodiments may include a pattern of circuitry, components and Energy Sources which are small enough to not adversely affect the sight of the Ophthalmic Lens wearer and therefore the Media Insert 220 may locate them within, or exterior to, an Optical Zone 210.

Reference has been made to electronic circuits making up part of the componentry of Ophthalmic Devices incorporating a neural frequency detection system. In some embodiments according to aspects of the disclosure, a single and/or multiple discrete electronic devices may be included as discrete chips, for example, in the ophthalmic Media Inserts. In other embodiments, the energized electronic elements can be included in the Media Insert in the form of Stacked Integrated Components. Accordingly and referring now to FIG. 3, a schematic diagram of an exemplary cross section of a Stacked Integrated Components Media Insert implementing a neural frequency detection system is depicted. In particular, the Media Insert may include numerous layers of different types which are encapsulated into contours consistent with the ophthalmic environment that they will occupy. In some embodiments, these Media Inserts with Stacked Integrated Component layers may assume the entire annular shape of the Media Insert. Alternatively in some cases, the Media Insert may be an annulus whereas the Stacked Integrated Components may occupy just a portion of the volume within the entire shape.

Referring back to FIG. 3, there may be thin film batteries 330 used to provide Energization used to operate the neural frequency detection system 310. In some embodiments, these thin film batteries 330 may comprise one or more of the layers that can be stacked upon each other with multiple components in the layers and interconnections therebetween.

Figure 3:
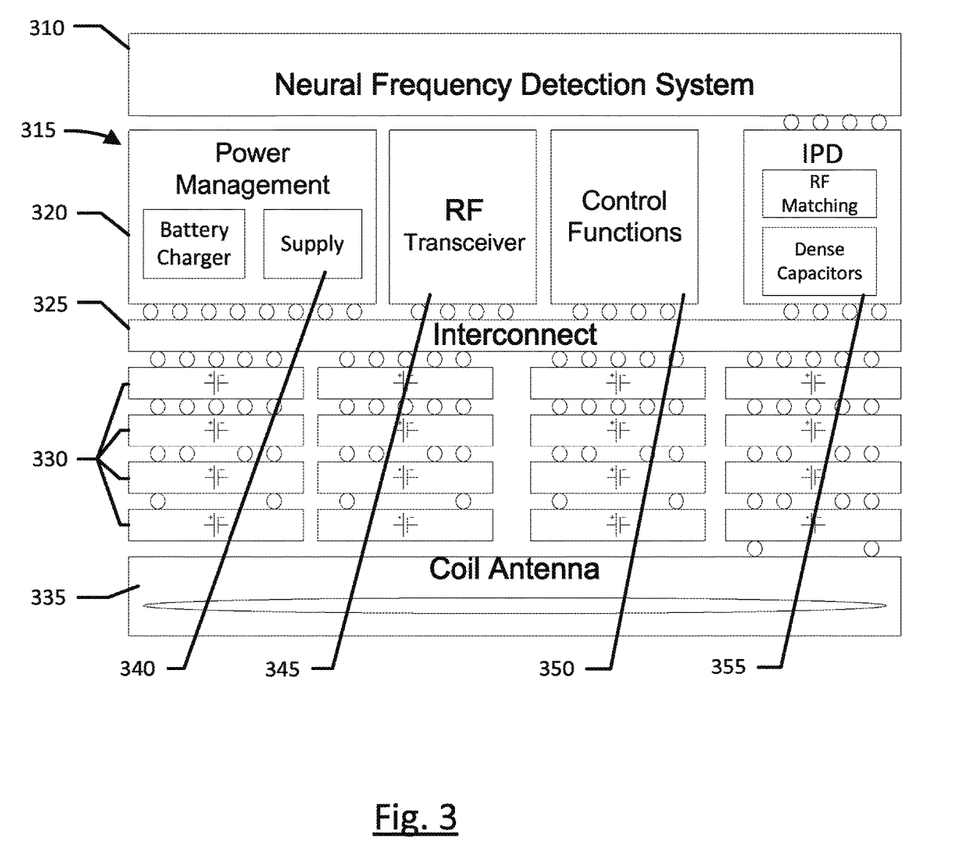
FIG. 3 is a schematic diagram of an exemplary cross section of a Stacked Die Integrated Components Media Insert implementing a neural frequency detection system in accordance with aspects of the present disclosure.

In some embodiments, there may be additional interconnections between two layers that are stacked upon each other. In the state of the art there may be numerous manners to make these interconnections; however, as demonstrated the interconnection may be made through solder ball interconnections between the layers. In some embodiments only these connections may be required; however, in other cases the solder balls may contact other interconnection elements, as for example with a component having through layer vias.

In other layers of the Stacked Integrated Component Media Insert, a layer 325 may be dedicated for the interconnections two or more of the various components in the interconnect layers. The interconnect layer 325 may contain, vias and routing lines that can pass signals from various components to others. For example, interconnect layer 325 may provide the various battery elements connections to a power management unit 320 that may be present in a technology layer 315. Other components in the technology layer 315 can include, for example, a transceiver 345, control components 350 and the like. In addition, the interconnect layer 325 may function to make connections between components in the technology layer 315 as well as components outside the technology layer 315; as may exist for example in the Integrated Passive Device 355. There may be numerous manners for routing of electrical signals that may be supported by the presence of dedicated interconnect layers such as interconnect layer 325.

In some embodiments, the technology layer 315, like other layer components, may be included as multiple layers as these features represent a diversity of technology options that may be included in Media Inserts. In some embodiments, one of the layers may include CMOS, BiCMOS, Bipolar, or memory based technologies whereas the other layer may include a different technology. Alternatively, the two layers may represent different technology families within a same overall family; as for example one layer may include electronic elements produced using a 0.5 micron CMOS technology and another layer may include elements produced using a 20 nanometer CMOS technology. It may be apparent that many other combinations of various electronic technology types would be consistent within the art described herein.

In some embodiments, the Media Insert may include locations for electrical interconnections to components outside the insert. In other examples, however, the Media Insert may also include an interconnection to external components in a wireless manner. In such cases, the use of antennas in an antenna layer 335 may provide exemplary manners of wireless communication. In many cases, such an antenna layer 335 may be located, for example, on the top or bottom of the stacked integrated component device within the Media Insert.

In some of the embodiments discussed herein, the battery elements 330 may be included as elements in at least one of the stacked layers themselves. It may be noted as well that other embodiments may be possible where the battery elements 330 are located externally to the stacked integrated component layers. Still further diversity in embodiments may derive from the fact that a separate battery or other Energization component may also exist within the Media Insert, or alternatively these separate energization components may also be located externally to the Media Insert.

Similarly, components of the neural frequency detection system 310 may be included in a Stacked Integrated Component architecture. In some embodiments, the neural frequency detection system 310 components may be attached as a portion of a layer. In other embodiments, the entire neural frequency detection system 310 may also comprise a similar configuration as the other Stacked Integrated Components.

Figure 4:
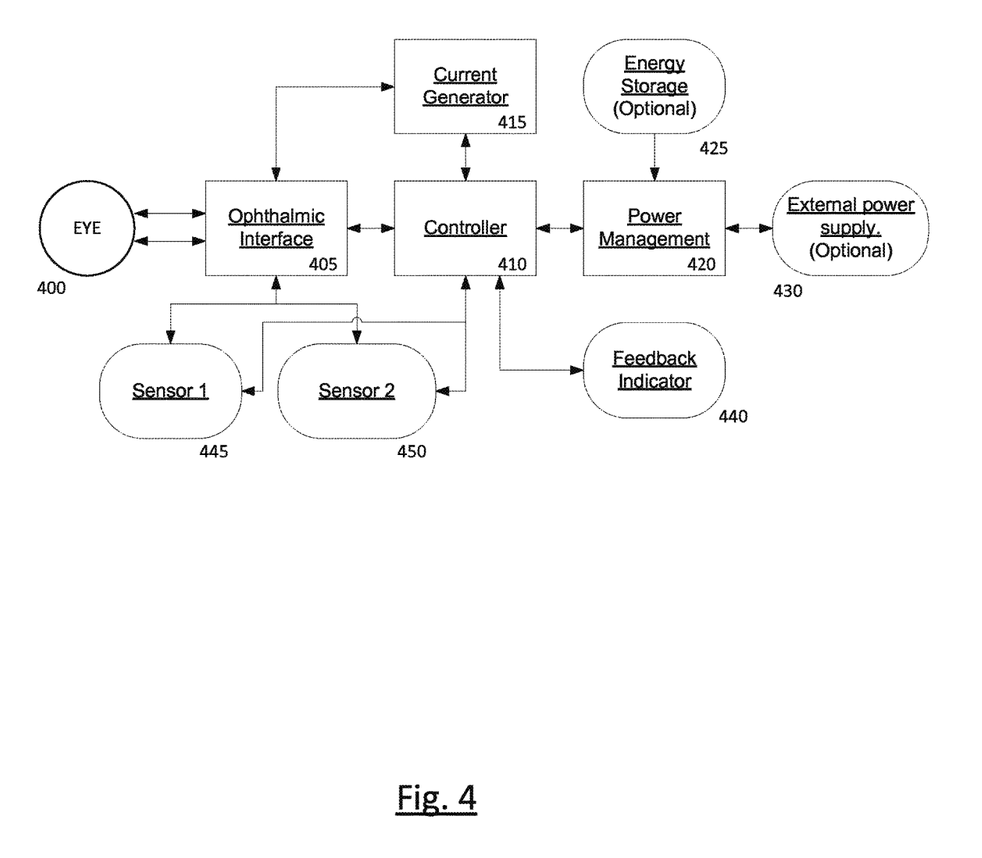
FIG. 4 is a schematic diagram of exemplary components that may be included in embodiments of the present disclosure.

Referring now to FIG. 4, a schematic diagram of exemplary components that may be included in embodiments of the present invention is depicted. At 400, the anterior ocular surface of an eye is represented. An Ophthalmic Device's Interface 405 may be placed onto the anterior ocular surface of the eye 400 to measure brainwave frequencies according to aspects of the disclosure. In some embodiments, the Ophthalmic Interface 405 may include or be in connection with one or more sensors 445 and 450 capable of detecting low band brainwaves that can be used to determine a brain function. The sensors 445 and 450 may be encapsulated and include contacts that may be coated with a biocompatible coating or polymer to prevent harm to the ocular surface. The determination of brain function may take place using the controller 410 in communication with the Ophthalmic Interface 405.

Figure 5:
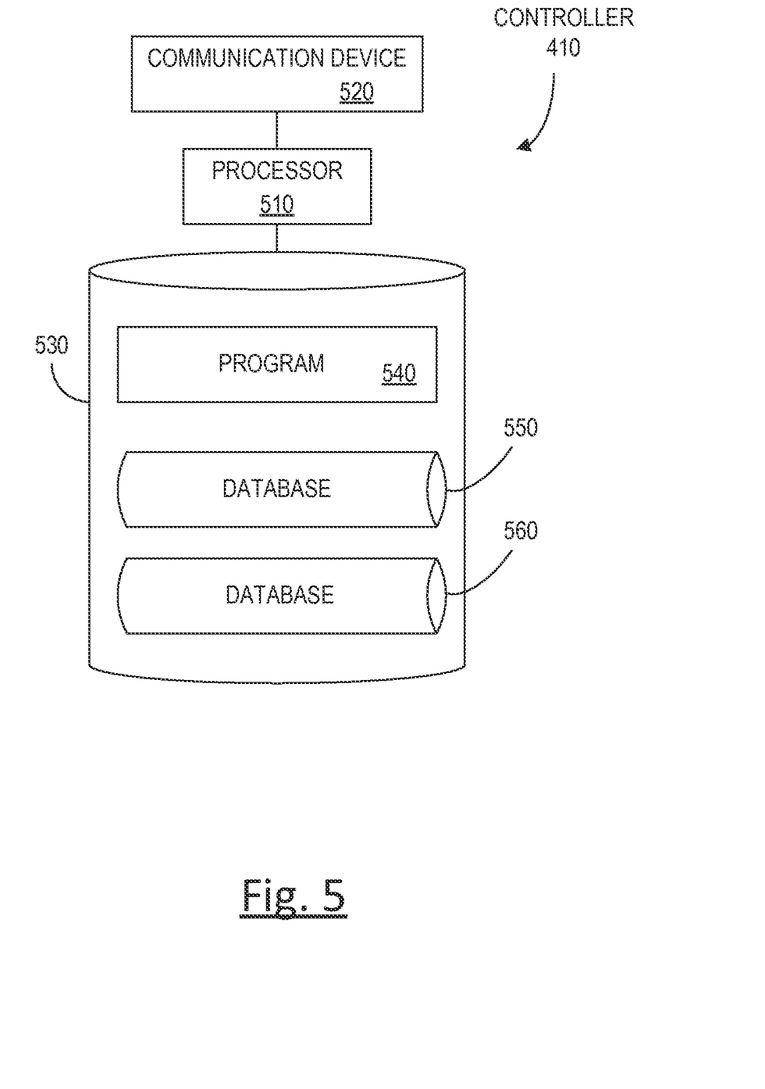
FIG. 5 is a schematic diagram of a controller that may be used to implement some aspects of the present disclosure.

The controller 410 may be, for example, one as described in FIG. 5, and may further comprise additional microcontroller(s), timer, signal conditioning device, state machine device, and/or event triggering device. Further, a current generator 415, a power management device 420 and a feedback indicator 440 may be in electrical communication with the controller 410. The current generator 415 can be capable of generating voltage-mode or current-mode. For example, DC or AC and different Waveforms and frequencies. The power management device 420 may include, for example a rectified, filter, voltage regulator and battery charger, and may be in communication with one or more of an energy storage device 425, and/or an external power supply 430. The external power supply 430 may include, for example solar cell, coil (inductive), antenna (RF), thermo-electric, piezoelectric, "Energy Harvesting", etc. The communication may be LED, inductive, EF, etc. The communication may occur with a device that may be positioned in proximity with the Ophthalmic Device, for example glasses, a wireless medical device, a cellular telephone, a personal computer, and the such.

The feedback indicator 440 may be a micro-electromechanical transducer capable of converting a digital signal to an acoustic output which can be delivered to the user through bone conduction. Bone conduction can be adequate based on the proximity of the eye to the skull through the eye socket, wherein the bones of the skull may be used to direct the sound to the cochlea of the inner ear. In addition or alternatively, in some embodiments, a visual feedback indicator 440 may be included in the Ophthalmic Device. The visual feedback indicator 440 may be a photon emitter projected towards the line of sight of the user wearing the device, for example. The photon emitter may include a light emitting diode (LED) and in some embodiments, an organic type of LED semiconductor device.

Depending on the power requirements, energy storage 425 may be necessary in some embodiments. As previously described, energy storage 425 means may include, for example, a battery (alkaline, Li-Ion, Li, Zn-air, etc.), a capacitor or a super capacitor embedded in the lens using for example SIC-Device technology.

Referring now to FIG. 5, a schematic diagram of a controller 410 that may be used in embodiments of the present disclosure is illustrated. The controller 410 can include one or more processors 510, which may include one or more processor components coupled to a communication device 520. In some embodiments, a controller 410 can be used to transmit energy to the Energy Source placed in the Ophthalmic Device. The processors 510 can be coupled to a communication device 520 configured, for example, to communicate energy via a communication channel.

In addition, the communication device 520 may be used to electronically communicate with components forming part of the communication channel within the Media Insert, for example. The communication device 520 may also be used to communicate with an external wireless device, for example, with one or more controller apparatus or programming/interface device components including a cellular device, personal computer, table, medical device, and the such.

The processor 510 is also in communication with a storage device 530. The storage device 530 may comprise any appropriate information storage device, including combinations of magnetic storage devices, optical storage devices, and/or semiconductor memory devices such as Random Access Memory (RAM) devices and Read Only Memory (ROM) devices.

The storage device 530 can store a program 540 for controlling the processor 510. The processor 510 performs instructions of a software program 540, and thereby operates in accordance with the present invention. For example, the processor 510 may output an electrical signal to provide an indication to the user according to a brain function determination. The determination of a brain function taking place at a particular point in time may occur using stored, in one or more databases 550 and 560 of the storage device 530, brain frequency profiles descriptive of brain function/activity according to brainwave frequencies. Accordingly, the database may also include parameters and controlling algorithms for the control of the neural frequency system components that may reside in the Ophthalmic Device as well as data and/or measured feedback that can be used to tailor the brain activity profiles for the particular user. In some embodiments, that data may be ultimately communicated to/from an external wireless device which may also be capable of providing feedback to the user.

Figure 6:
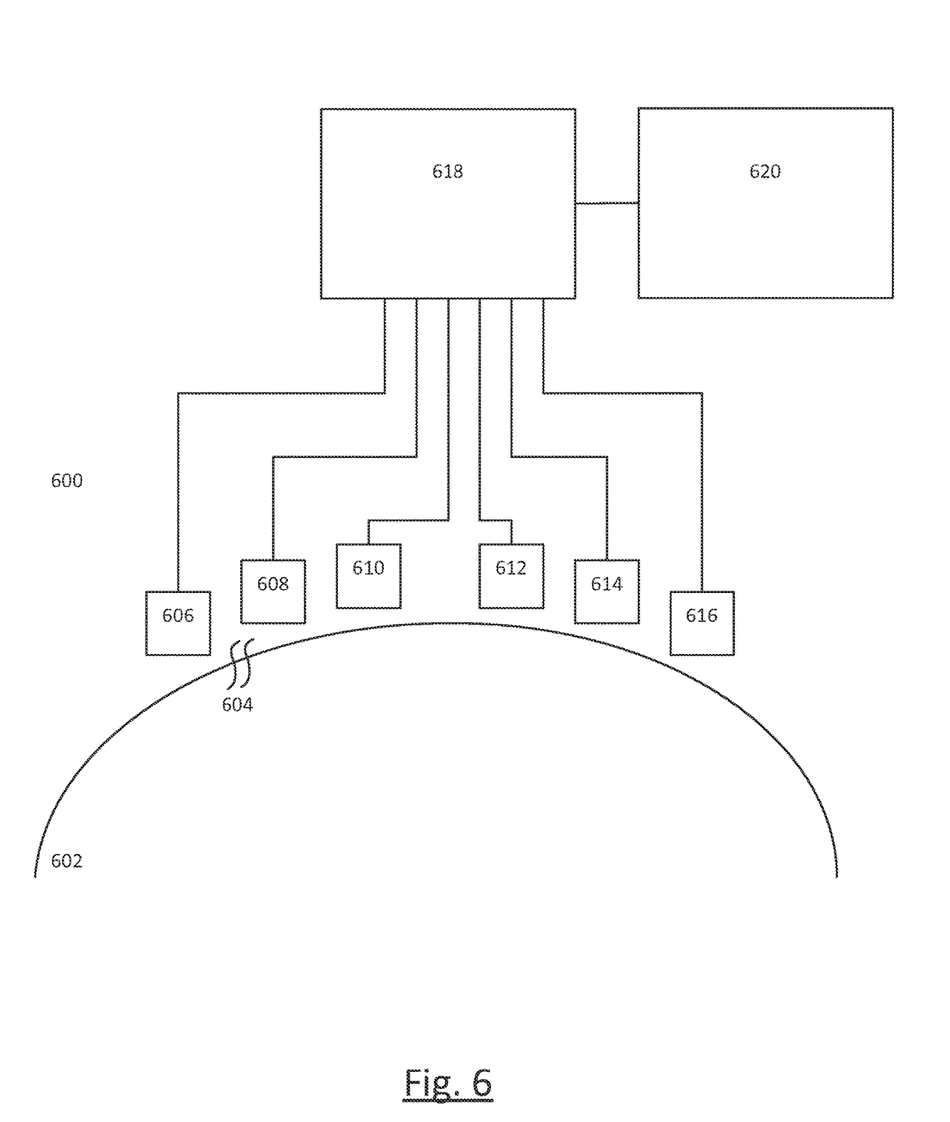
FIG. 6 is an exemplary schematic diagram of a neural frequency detection system for detecting brainwave frequencies according to aspects of the present disclosure.

Referring now to FIG. 6, an exemplary circuit schematic diagram of a neural frequency detection system 600 is depicted. Contacts 606, 608, 610, 612, 614, and 616 may provide electrical contact with an ocular surface 602 through biocompatible means as previously discussed. Switching network 618 can allow generator and/or sensor circuitry 620 to connect to certain sensors, for example adjacent pairs. The system may first measure the difference in potential between contacts 606 and 608. The system may then measure 608 and 610, 610 and 612, 612 and 614, and 614 and 616. For example, by detecting a measurable difference which can exist between contacts due to brain activity emitting low band frequencies, e.g. neural frequency 604. This model may be extended with a multi-dimension grid or other arrangement of contacts, to provide for more accurate analysis of brainwave activity.

Figure 7:
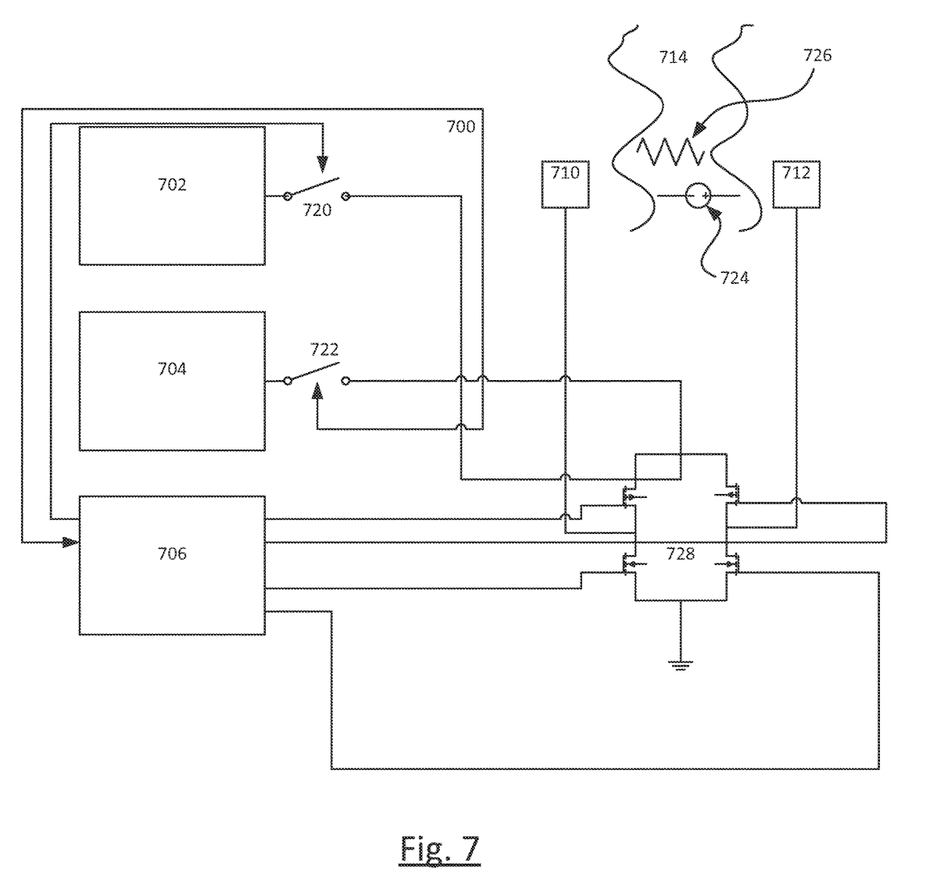
FIG. 7 is another exemplary circuit schematic diagram of a neural frequency detection system according to aspects of the present disclosure.

Referring now to FIG. 7, another exemplary circuit schematic diagram of a neural frequency detection system according to aspects of the present disclosure is depicted. A voltage source 724 is depicted which may also be used to measure resistance or change in a frequency emitted by the system 700. The measurable resistance 726 can be measured on the tissue of the ocular surface and/or the conductive ocular fluid. Contacts 710 and 712 may be positioned on the ocular surface and, as previously discussed, may be of appropriate biocompatible, conductive materials or encapsulated by biocompatible conductive materials. Contacts 710 and 712 may connect to a switching network 728, shown as an H-bridge, a common circuit known in the field of electronics, which may permit connecting, disconnecting, and toggling the polarity of applied or measured voltage and current. Controller 706 may control the switching network 728 along with switches 720 and 722. The switches may be implemented with MOSFET devices, as is common in the industry. The controller may be implemented as a microcontroller, for example. Switch 720 may connect to generator block 702 to the switching network 728. This generator block 702 can contain the circuitry necessary to generate the voltage, current, waveforms, and frequencies desired for brain frequency analysis. Switch 722 may connect sensor block 704 to the switching network 728. The sensor block 702 may detect wavelengths and amplitudes parameters of neural emitted frequencies 714.

In one system state, for example, switch 722 may be closed while switch 720 may be open, and the desired switches in switching network 728 may be enabled and disabled to connect the sensor 704 to the neural frequency 714 through contacts 710 and 712 without connecting the generator 702.

Sensor 704 may be designed to measure voltage with techniques common in the electronics industry, for example a differential or instrumentation amplifier. Sensor 704 may also be configured as a capacitance sensor, resistance sensor, or other electrical sensor. In another system state, switch 720 may be closed while switch 722 may be left open. Generator 702 may be operated as a controlled voltage source, controlled current source, or an AC generator to promote or amplify a signal.

Figure 8:
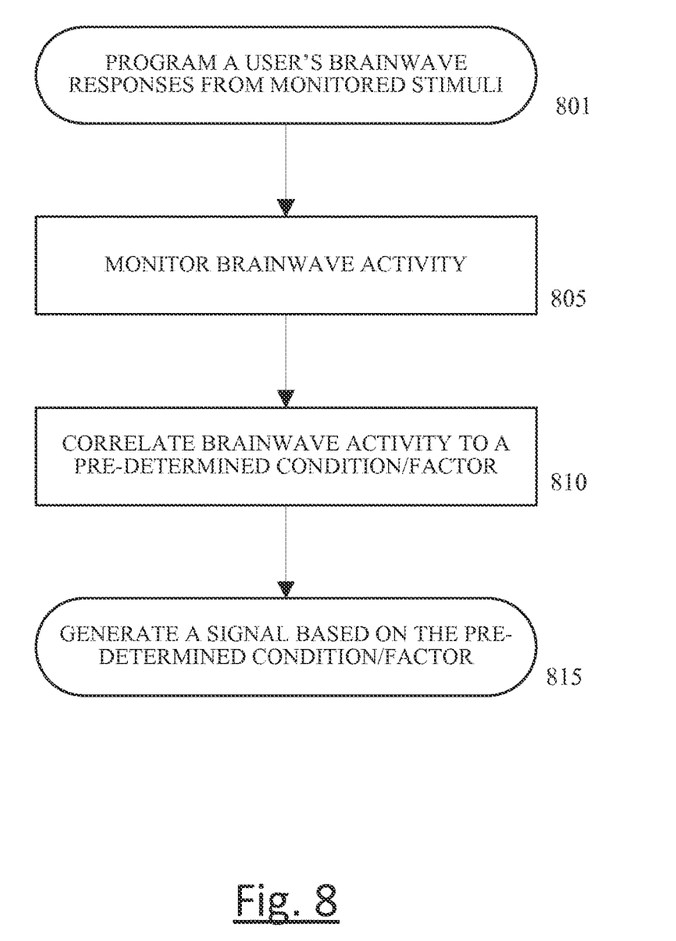
FIG. 8 illustrates exemplary method steps that may be used to implement the neural frequency detection system of the ophthalmic device according to aspects of the present disclosure.

Referring now to FIG. 8, a flowchart with exemplary method steps that may be used to implement the neural frequency detection system of the ophthalmic device is illustrated. Beginning at step 801, a user's brainwave activity can be programmed in a database. In some embodiments, the database may be included in the neural frequency detection system of the Ophthalmic Device or it may be programmed using an external device. The programming brainwave activity can include exposing a user to a number of controlled conditions/stimuli and measuring the brain function/activity resulting from each. Using this data, different neural frequency profiles corresponding to each controlled condition/stimuli can be programmed to correlate the frequencies to specific brain activity/functions. Functions detected in the frontal lobe part of the brain can include those controlled mostly by the dopamine-sensitive neurons in the cerebral cortex which relate a person's attention, reward, short-term memory tasks, planning, and motivation can be made.

At step 805, brainwave activity/function is monitored using the Ophthalmic Device of the present disclosure. Monitoring of brain activity can include correlating the measured frequencies to pre-determined brain activity/functions recorded in the database. The profile for each brain activity/function can include threshold levels for neural frequencies specific to the user or generic depending on the condition. The monitoring of brain activity may occur upon demand from a user, at a specific frequency, or once a condition has been detected. For example, in some embodiments, the monitoring of brain activity may occur once a compatible wireless device is within a predetermined distance from the Ophthalmic Device. In some embodiments, the monitoring frequency and use may depend on the type of Ophthalmic embodiment, use and energy source limitations.

At step 810, using the neural frequency profiles, the monitored frequencies can be correlated to one or more pre-determined brain function/activity. Based on the correlation, at step 815, a signal can be outputted by the processor. In some embodiments, the signal can be translated into a mechanical vibration by an electromechanical transducer to generate an audible signal as previously described. In other embodiments, the signal may be translated by a visual signal produced by a photon emitter. In yet additional embodiments, the signal may be sent to a wireless device in wireless communication with the Ophthalmic Device. Transmission of information can occur wirelessly, for example, via an RF frequency, a local area network (LAN), and/or a private area network (PAN), depending on the communication device and functionality implemented. The signal records may be maintained as part of a user's history, to prevent sending duplicate messages, and/or for prioritization/optimization of future message, for example.

The many features and advantages of the invention are apparent from the detailed specification, and thus, it is intended by the appended claims to cover all such features and advantages of the invention which fall within the true spirit and scope of the invention. Further, because numerous modifications and variations will readily occur to those skilled in the art, it is not desired to limit the invention to the exact construction and operation illustrated and described, and accordingly, all suitable modifications and equivalents may be resorted to, falling within the scope of the invention.

The invention claimed is:

1. An ophthalmic device with neural frequency detection comprising:
   a media insert comprising a front and back arcuate surface forming a cavity therebetween that contains an energy source, a controller, a transmitter, and a neural frequency detection system,
   wherein the energy source, the controller, the transmitter, and the neural frequency detection system are located outside of an optical zone of the ophthalmic device,
   wherein the energy source energizes the controller,
   wherein the controller comprises a processor in digital communication with a digital media storage device,
   wherein the neural frequency detection system comprises one or more sensors capable of measuring neural frequencies of a wearer of the ophthalmic device;
   wherein the transmitter transmits the measured neural frequencies to the processor, and
   wherein the processor receives said measured neural frequencies and detects a brain function based on pre-recorded data stored in the digital media storage device.

2. The ophthalmic device of claim 1, additionally comprising:
   a radio frequency antenna capable of transmitting data from and to an external wireless device.

3. The ophthalmic device of claim 2, wherein the processor sends a signal to the external wireless device according to the detected brain function.

4. The ophthalmic device of claim 2, additionally comprising:
   a photon emitter capable of providing a visual signal to the wearer of the ophthalmic device.

5. The ophthalmic device of claim 4, wherein the processor receives a signal based on the brain function of a user of said external wireless device through the radio frequency antenna and provides said visual signal to the wearer of the ophthalmic device through the photon emitter.

6. The ophthalmic device of claim 5, wherein the visual signal is provided to the wearer of the ophthalmic device when the signal from the brain function of said user of said external wireless device is equivalent to the signal from the brain function of the wearer of the ophthalmic device receiving the visual signal.

7. The ophthalmic device of claim 6, wherein the external wireless device is another ophthalmic device being worn by said user.

8. The ophthalmic device of claim 2, additionally comprising:
   an electromechanical transducer capable of emitting an audible signal and providing said audible signal to the wearer of the ophthalmic device.

9. The ophthalmic device of claim 8, wherein the processor receives a signal based on the brain function of a user of said external wireless device through the radio frequency antenna and provides an audible signal to the wearer of the ophthalmic device through the electromechanical transducer.

10. The ophthalmic device of claim 9, wherein the audible signal is provided to the wearer of the ophthalmic device when the signal from the brain function of said user of said external wireless device is equivalent to the signal to the brain function of the wearer of the ophthalmic device receiving the audible signal.

11. The ophthalmic device of claim 10, wherein the external wireless device is another ophthalmic device being worn by said user.

12. The ophthalmic device of claim 1, wherein the energy source is fabricated using stacked integrated component device technologies.

13. A method of detecting brain activity comprising:
   providing an ophthalmic device comprising a media insert containing a neural frequency detection system, an energy source, a transmitter, and a controller, wherein the controller comprises a processor in digital communication with a digital media storage device, and wherein the neural frequency detection system comprises one or more sensors capable of measuring neural frequencies of a wearer of the ophthalmic device;

recording, in the digital media storage device, neural frequency profiles corresponding to a plurality of brain functions;

placing the ophthalmic device on an eye of the wearer;

measuring the neural frequencies of the wearer of the ophthalmic device through the one or more sensors of the neural frequency detection system;

transmitting a signal to the processor based on the measured neural frequencies of the wearer of the ophthalmic device; and detecting a brain function of the wearer of the ophthalmic device by comparing the measured neural frequencies with said neural frequency profiles recorded in the digital media storage device.

14. The method of claim 13, additionally comprising the step of:

sending a signal to an external wireless device according to the detected brain function.

15. The method of claim 14, wherein the external wireless device is one or more of a cellular device, a biomedical device, a drug dispensing device, a tablet, and a personal computer.

16. The method of claim 13, wherein the ophthalmic device additionally comprises a photon emitter.

17. The method of claim 16, additionally comprising the step of:

providing a visual signal to the wearer of the ophthalmic device through the photon emitter.

18. The method of claim 13, wherein the ophthalmic device additional comprises an electromechanical transducer.

19. The method of claim 18, additionally comprising the step of:

providing an audible signal to the wearer of the ophthalmic device through the electromechanical transducer.

20. A method of detecting brain activity comprising:

providing an ophthalmic device comprising a neural frequency detection system, an energy source, a transmitter and a controller, wherein the controller comprises a processor in digital communication with a digital media storage device, and wherein the neural frequency detection system comprises one or more sensors capable of measuring neural frequencies of a wearer of the ophthalmic device;

recording, in the digital media storage device, neural frequency profiles corresponding to brain functions or activities, wherein the neural frequency profiles are specific to the wearer of the ophthalmic device;

placing the ophthalmic device on an eye of the wearer;

measuring the neural frequencies of the wearer of the ophthalmic device through the one or more sensors of the neural frequency detection system;

transmitting a signal to the processor based on the measured neural frequencies of the wearer; and detecting a brain function or activity of the wearer of the ophthalmic device by comparing the measured neural frequencies with said neural frequency profiles recorded in the digital media storage device.

* * * * *